(12) United States Patent
Ding et al.

(10) Patent No.: US 10,640,381 B2
(45) Date of Patent: May 5, 2020

(54) METHOD FOR POLYMER REMOVAL FROM SINGLE-WALLED CARBON NANOTUBES

(71) Applicant: NATIONAL RESEARCH COUNCIL OF CANADA, Ottawa (CA)

(72) Inventors: Jianfu Ding, Orleans (CA); Zhao Li, Orleans (CA); Patrick Roland Lucien Malenfant, Orleans (CA)

(73) Assignee: National Research Council of Canada, Ottawa (CA)

( * ) Notice: Subject to any disclaimer, the term of this patent is extended or adjusted under 35 U.S.C. 154(b) by 195 days.

(21) Appl. No.: 15/618,242

(22) Filed: Jun. 9, 2017

(65) Prior Publication Data
US 2018/0354799 A1      Dec. 13, 2018

(51) Int. Cl.
*C01B 32/159*        (2017.01)
*C08F 32/08*        (2006.01)
(Continued)

(52) U.S. Cl.
CPC ............ *C01B 32/159* (2017.08); *C08F 32/08* (2013.01); *C08F 36/04* (2013.01); *B82Y 30/00* (2013.01);
(Continued)

(58) Field of Classification Search
CPC ... C01B 32/159; C01B 2202/02; C08F 36/04; C08F 32/08; C07D 213/06; C07C 211/02; B82Y 30/00
See application file for complete search history.

(56) References Cited

U.S. PATENT DOCUMENTS 6,331,262 B1    12/2001    Haddon et al.
7,226,818 B2     6/2007    Malenfant et al.
(Continued)

FOREIGN PATENT DOCUMENTS

WO      2015024115 A1    2/2015

OTHER PUBLICATIONS

Lei, Ting, et al. "Removable and recyclable conjugated polymers for highly selective and high-yield dispersion and release of low-cost carbon nanotubes." Journal of the American Chemical Society 138.3 (2016): 802-805.*
(Continued)

*Primary Examiner* — Richard M Rump
(74) *Attorney, Agent, or Firm* — Aventum IP Law LLP

(57) ABSTRACT

Processes for selectively dispersing semi-conducting single-walled carbon nanotubes (sc-SWCNTs) in a solvent. One process comprises adding an amine either: to a conjugated polymer extraction process (CPE) of the sc-SWCNTs; or after the CPE of the sc-SWCNTs, in which the amine partially displaces the conjugate polymer associated with the sc-SWNTs dispersed in the solvent. Another process comprises adding an amine either: to a conjugated polymer extraction process (CPE) of the sc-SWCNTs; or after the CPE of the sc-SWCNTs, with the proviso that the amine excludes EDTA. Also, a process for displacement of a conjugated polymer from the surface of semi-conducting single-walled carbon nanotubes (sc-SWCNTs) dispersed in a solvent, which comprises adding an amine either: to a conjugated polymer extraction process (CPE) of the sc-SWCNTs; or after the CPE of the sc-SWCNTs.

17 Claims, 8 Drawing Sheets

(51) Int. Cl.
　　　*C08F 36/04*　　(2006.01)
　　　*B82Y 30/00*　　(2011.01)
　　　*C07C 211/02*　　(2006.01)
　　　*C07D 213/06*　　(2006.01)
　　　*B82Y 40/00*　　(2011.01)

(52) U.S. Cl.
　　　CPC ........... *B82Y 40/00* (2013.01); *C01B 2202/02* (2013.01); *C07C 211/02* (2013.01); *C07D 213/06* (2013.01)

(56) References Cited

U.S. PATENT DOCUMENTS

| | | |
|---|---|---|
| 7,250,569 B2 | 7/2007 | Sun et al. |
| 8,231,854 B2 | 7/2012 | Kajiura et al. |
| 2010/0278714 A1 | 11/2010 | Tanaka et al. |
| 2012/0104328 A1 | 5/2012 | Park et al. |

OTHER PUBLICATIONS

Ding, Jianfu et al—"Synthesis and Characterization of Alternating Copolymers of Fluorene and Oxadiazole"; Macromolecules 2002, 35, pp. 3474-3483.

Ding, Jianfu et al—"Enrichment of large-diameter semiconducting SWCNTs by polyfluorene extraction for high network density thin film transistors"; Royal Society of Chemistry, Nanoscale 2014, 6, pp. 2328-2339.

Ding, Jianfu et al—"A hybrid enrichment process combining conjugated polymer extraction and silica gel adsorption for high purity semiconducting single-walled carbon nanotubes (SWCNT)"; Royal Society of Chemistry, Nanoscale 2015, 7, pp. 15741-15747.

Gao, J. et al—"Effectiveness of sorting single-walled carbon nanotubes by diameter using polyfluorene derivatives"; ScienceDirect Carbon 49, 2011, Elsevier 2010; doi:10.1016/j.carbon.2010.09.036, pp. 333-338.

Hersam, Mark. C.—"Progress towards monodisperse single-walled carbon nanotubes", Nature nanotechology, vol. 3, Jul. 2008; Review Article; pp. 387-394.

Hwang, J-Y. et al—"Polymer Structure and Solvent Effects on the Selective Dispersion of Single-Walled Carbon Nanotubes"; JACS Articles; published on Web Feb. 23, 2008; ACS 2008, pp. 3543-3553.

Naumov, Anton V. et al—"Analyzing Absorption Backgrounds in Single-Walled Carbon Nanotube Spectra"; ACS Nano, 2011, vol. 5, No. 3, pp. 1639-1648.

Samsonidze, G. G. et al—"Quantitative evaluation of the octadecylamine-assisted bulk separaton of semiconducting and metallic single-wall carbon nanotubes by resonance Raman spectroscopy", Applied Physics Letters, vol. 85, No. 6, Aug. 2004, p. 1006-1008.

\* cited by examiner

METHOD FOR POLYMER REMOVAL FROM SINGLE-WALLED CARBON NANOTUBES

FIELD

The present application relates to carbon nanotubes. In particular, the present application relates to purification of single-walled carbon nanotubes.

BACKGROUND

The background description includes information that may be useful in understanding the present invention. It is not an admission that any of the information provided herein is prior art or relevant to the presently claimed invention, or that any publication specifically or implicitly referenced is prior art.

An important class of carbon nanotubes is single-walled carbon nanotubes (SWCNTs). They are generally produced as ensemble samples containing both metallic (m-SWCNTs) and semiconducting (sc-SWCNTs) nanotubes with a distribution of chiralities centered at a mean diameter. Several methods can be used to produce SWCNTs which will vary in the distribution of chiralities, diameter range, semiconducting/metallic (sc/m) content and average length. For many applications, such as thin film transistors (TFTs), a sc-purity higher than 99% is needed.

Several methods have been used to demonstrate the effective enrichment and isolation of sc-SWCNTs with greater than 99% sc-purity as assessed by absorption spectroscopy. Among these methods are density gradient ultracentrifugation (DGU), gel chromatography (GC), dielectrophoresis and selective extraction by conjugated polymers. Amongst these listed options, the simplicity of the conjugated polymer extraction (CPE) process, which generally entails a dispersion followed by a centrifugation step, further distinguishes it from the rest as a cost-effective method for the isolation of sc-SWCNTs with greater than 99% semiconducting content.

The first disclosure that conjugated polymers could selectively disperse semiconducting SWCNTs and lead to enriched semiconducting SWCNT fractions of relevance for thin film transistor fabrication can be found in the patent literature (Malenfant 2007). Subsequently, the exceptional selectivity that could be achieved with polyfluorene derivatives towards specific semiconducting SWCNT chiralities was demonstrated. More recently an effective enrichment of HiPco sc-SWCNTs using poly(3-dodecyl thiophene) (P3DDT) and arc-plasma-jet tubes using PFDD was also demonstrated to provide TFTs with mobilities greater than 10 cm2/Vs. Collectively, these results, amongst others, have clearly shown the potential for conjugated polymers in sc-SWCNT enrichment and TFT device fabrication.

To date, many homo- and copolymers of phenylenevinylene, carbazole, thiophene and fluorene have been investigated for enrichment. For example, P3DDT displayed a promising result in the separation of HiPCO nanotubes, however P3DDT is not suitable for the separation of larger diameter SWCNTs, which are more desirable when trying to minimize contact resistance and to obtain a large electron mobility in thin film transistors. Similarly, it has been observed that poly(9,9-dioctylfluorene) (PFO) has a high selectivity in dispersing small-diameter sc-SWCNTs with large chiral angles ($20°≤0≤30°$), but not large-diameter SWCNTs, which is believed to be difficult to disperse and to enrich owing to the strong interaction between the nanotubes associated with the low curvature of the nanotube wall. As a result, co-monomer units have been introduced into the polyfluorene main chain in order to target specific tube chiralities/diameters. They include: phenylene-1,4-diyl, thiophen-2,5-diyl, anthracene-9,10-diyl, anthracene-1,5-diyl, naphthalene-1,5-diyl, 2,2-bithiophene-5,5'-diyl, and benzo-2,1,3-thiadiazole-4,7-diyl.

Furthermore, the length of the side alkyl chain of the polymers has a significant impact on the enrichment effectiveness. Polymers with 12-carbon long side chains showed an improved selectivity to sc-SWCNTs with larger diameters. Recently work on the enrichment of large diameter SWCNTs using fluorene homopolymers with long alkyl side chains has been done, which achieved a device performance of 14.3 cm2/Vs and on/off ratio over $10^5$.

The basic CPE process is described in, for example, WO 2015/024115 and J. Ding et al. (Enrichment of large-diameter semiconducting SWCNTs by polyfluorene extraction for high network density thin film transistors, *Nanoscale*, 2014, 6, 2328-2339), both of which are incorporated herein by reference.

CPE and its deduced hybrid process (disclosed, for example, in WO 2015/024115) have proved to be an efficient technique for a large scale sc-SWCNTs enrichment at a purity higher than 99.9%. However, removal of the polymer that wraps and disperses the SWCNTs is a tedious process.

One method is the use of excess polymer to boost the yield of the CPE process. However, this leads to long filtration times (for example, it takes more than 24 h to filter 1 L of sample having 50 mg of SWCNTs), along with higher polymer/tube rations in the final product. Removal of the excess polymer typically requires long soaking treatments in solvent, followed by additional filtration, which is both unproductive and costly.

US 2012/0104328 discloses a conjugated polymer (CP) process for selectively separating sc-SWCNT from m-SWCNT. The conjugated polymers are polythiophenes. Paragraph [0093] indicates that an additive may be used to improve separation efficiency and that the additive can be ethylene diamine tetraacetic acid (EDTA).

Gao J, et al. *Carbon*. 49(1), January 2011, 333-338. discloses the use of amine-functionalized polyfluorenes, specifically a dimethyl amino-substituted polyfluorene, in the extraction of sc-SWCNT. The amine-substituted polymer provides: better solubility (faster dissolution) of the SWCNT than PFO; higher total amounts of dispersed SWCNT; and a lower ratio of CP to CNT, reducing the ratio from 15:1 (found with PFO) to a ratio in a range of 10:1 to 1:1.

A number of publications (U.S. Pat. Nos. 7,250,569; 6,331,262; 8,231,854; 2010/0278714; Hersam M. C., *Nature Nanotechnology*, Vol. 3, July 2008, 387-394; Hwang J-Y, et al. *J. Am. Chem. Soc.* 130(11), 2008, 3543-3553; and Samsonidze G. et al. *Applied Physics Letters*, 85(6), August 2004, 1006-1008) disclose that amines of various sorts can be used to aid in the selective separation of SWCNT or in the solubilisation of SWCNT. However, none of these documents disclose that the amine can be used in a CPE process.

There is a need for an improvement in a CPE process that selectively disperses sc-SWCNT in a solvent, so as to facilitate removal of the conjugate polymer that wraps and disperses the sc-SWCNTs.

SUMMARY

The proposed invention is directed to an improvement in a conjugate polymer (CP) extraction process for selectively dispersing sc-SWCNTs in a solvent. It is now proposed to use an amine additive for displacement of excess conjugate polymer from the sc-SWCNT surface.

The proposed invention is a modification of the hybrid process disclosed in WO 2015/024115 and Ding J, et al. *Nanoscale*. 2014, 6, 2328. The modification contemplates the use of an amine added during, or after, the extraction step in order to increase yield of the sc-SWCNT and remove conjugated polymer.

In one aspect of the present invention, there is provided a process for selectively dispersing semi-conducting single-walled carbon nanotubes in a solvent, the process comprising adding an amine either: a) to a conjugated polymer extraction process of the sc-SWCNTs; or b) after the CPE of the sc-SWCNTs, wherein the amine partially displaces the conjugate polymer associated with the sc-SWNTs dispersed in the solvent.

In a further aspect of the present invention, there is provided a process for selectively dispersing semi-conducting single-walled carbon nanotubes in a solvent, the process comprising adding an amine either: a) to a conjugated polymer extraction process of the sc-SWCNTs; or b) after the CPE of the sc-SWCNTs, with the proviso that the amine excludes EDTA.

In yet a further aspect of the present invention, there is provided a process for displacement of a conjugated polymer from the surface of semi-conducting single-walled carbon nanotubes dispersed in a solvent, the process comprising adding an amine either: a) to a conjugated polymer extraction process of the sc-SWCNTs; b) after the CPE of the sc-SWCNTs.

In any of the above processes, in step b), the amine may be added to the supernatant from the CPE. Furthermore, filtration of the sc-SWCNTs dispersed in the solvent can take less time than filtration of dispersed sc-SWNTs prepared by the CPE without the amine.

In any of the above processes, step a) may comprise: mixing raw single-walled carbon nanotubes (SWCNTs) with a conjugated polymer (CP) and an amine in the solvent to yield a solid phase and a liquid phase; and separating the solid phase from the liquid phase, wherein the liquid phase is enriched with the sc-SWCNTs.

In any of the above processes, the amine may be a non-functionalized amine. For example, the amine may be an alkylamine, such as (but not limited to) triethylamine, ethanol amine or pyridine. The amine may be triethylamine. The concentration of the amine in these processes can be from 1 ppm to 0.1% by weight, or from 0.001% to 0.05%.

In any of the above processes, the conjugated polymer may comprise a polyfluorene, a 9,9-dialkyl-substituted polyfluorene or a 9,9-diC8-36-alkyl-substituted polyfluorene. Alternatively, the conjugated polymer may comprise a polythiophene, a 3-alkyl-substituted polythiophene or a 3-C8-18-alkyl-substituted polythiophene. Or, the conjugated polymer may comprise a copolymer of 3-C10-18-alkyl-substituted thiophene with one or more comonomer units, the co-monomer comprising one or more of fluorene, bithiophene, phenylene, bipyridine, carbazole, anthracene, naphthalene or benzothiadiazole.

In any of the above processes, the conjugated polymer can have a number average molecular weight greater than about 10,000 Da, or a number average molecular weight from about 10,000 Da to about 30,000 Da.

In any of the above processes, the solvent may be a non-polar solvent, or may comprise an aromatic organic solvent. For example, the solvent may comprise toluene, benzene, ethyl benzene, xylenes, 1-methylnaphtalene or mixtures thereof. In particular, the solvent may comprise toluene.

The hybrid enrichment process comprises two-steps. The first step is based on selective dispersion and extraction of sc-SWCNTs using a conjugated polymer followed by a second step based on an adsorptive process in which the product of the first step is exposed to an inorganic absorptive medium to selectively bind predominantly m-SWCNTs, such that what remains dispersed in solution is further enriched in sc-SWCNTs. The first step produces an enriched sc-SWCNT dispersion with a moderated sc-purity (98%) at a high yield, or a high purity (99% and up) at a low yield. The second step not only enhances the purity of the polymer enriched sc-SWCNTs with a moderate purity, but also further promotes the highly purified sample to an ultra-pure level.

The mixture of sc-SWCNTs and m-SWCNTs may come from any convenient source of CNT preparation. Such starting material preferably comprises raw (about 0.6 to 2.2 nm average diameter) SWCNTs prepared from HiPco, CoMoCAT, CVD, arc-discharge, laser-ablation or plasma processes. The amount of conjugated polymer used in the extraction in relation to the amount of SWCNTs in the mixture of sc-SWCNTs and m-SWCNTs (i.e. polymer: SWCNT mass ratio) can be about 0.5:1, or from 0.1:1 to 10:1.

The conjugated polymer may comprise any suitable polymer that will selectively fractionate sc-SWCNTs from the starting mixture. The polymer may be a homopolymer or copolymer. Some examples of polymers include polyfluorenes, polythiophenes, polyphenylenevinylenes, and their copolymers with one or more co-monomer units (e.g. bithiophene, phenylene, bipyridine, anthracene, naphthalene and benzothiadiazole) or combinations thereof. The conjugated polymer may comprise a polyfluorene derivative, for example a 9,9-dialkyl-substituted polyfluorene, or a 9,9-diC8-36-alkyl-substituted polyfluorene, or a 9,9-diC10-18-alkyl-substituted polyfluorene. The alkyl substituent may be linear or branched. The conjugated polymer can have a number average molecular weight ($M_n$) greater than about 8,000 Da, for example from about 10,000 Da to about 500,000 Da; or, for example, from about 10,000 Da to about 30,000 Da. The combination of the π π interaction between the conjugated polymer and the nanotubes, and the wrapping/coating of the conjugated polymer on the nanotubes affords a high selectivity based on the electronic properties and chiralities of the nanotubes. Furthermore, the selective polymer wrapping/coating enables the dispersion of individual SWCNTs to afford a good separation between m-/sc-nanotubes. This feature provides a path towards high purity which will be required for many electronic device applications. In addition, the composition and architecture of the polymer side chains can be adjusted to balance the solubilisation and the interaction with the nanotubes to optimize the selectivity. Also, the molecular design of the polymer main-chain can provide the conjugated polymer a unique interaction with the nanotubes as well as some other desired properties.

In order to enhance the selectivity, extracting with the conjugated polymer may be accomplished in a non-polar solvent. The mixture of sc-SWCNTs and m-SWCNTs may be dispersed in the solvent in the presence of the conjugated polymer. The mixture of se-SWCNTs and m-SWCNTs may be dispersed in the solvent at a concentration of from about 0.1 mg/mL to about 10.0 mg/mL; also from about 0.4 mg/mL to about 2.0 mg/mL, with a polymer/SWCNT ratio of 0.1:1 to 10:1. The polymer/SWCNT ratio can impact the extraction yield and sc-purity. A high ratio often produces a high yield but a low purity. Formation of the dispersion may be assisted by known techniques in the art, for example, sonication, mechanical agitation and the like. Subsequent separation of the well-dispersed SWCNTs from the poorly-dispersed SWCNTs collects polymer-coated SWCNTs in the dispersion, while poorly-dispersed SWCNTs are removed which may contain tubes coated with less polymer, nanotube bundles, carbon and catalyst impurities. The subsequent separation may be accomplished by any suitable method, for example centrifugation, filtration and the like, or any combination thereof. Centrifugation is preferred. Such centrifugation typically yields sediment and supernatant, the sediment having gravitated to the bottom of a centrifuge tube and the supernatant being the liquid on top. The sediment is enriched in m-SWCNTs and the supernatant is enriched in sc-SWCNTs, relative to the starting mixture. The conjugated polymers possess a similar tendency to interact with the sc- and m-SWCNTs, while m-SWCNTs have a stronger capability to form bundles with other tubes, and thus the SWCNTs remaining in the dispersion (e.g. in the supernatant) after separation are enriched in sc-SWCNTs, while the SWCNTs separated from the dispersion (e.g. in the sediment) are enriched in m-SWCNTs. Further extraction processes can be applied to the sediment and the resulting combination dispersion will give a higher yield of sc-SWCNTs.

The dispersion containing polymer-coated SWCNTs enriched in sc-SWCNTs may be exposed directly to the inorganic adsorptive medium, or further processing may be performed prior to contacting the enriched sc-SWCNT dispersion with the inorganic adsorptive medium. The further processing may be, for example: isolating the polymer-coated SWCNTs from the dispersion by filtration and, washing and then re-dispersing the polymer-coated enriched sc-SWCNTs to form an enriched sc-SWCNT dispersion. Filtration and washing of the enriched sc-SWCNTs can remove excess polymer which is not attached to SWCNTs, thus allowing a polymer:SWCNT stoichiometry to be adjusted.

In the second step of the hybrid process, the enriched sc-SWCNT dispersion is exposed to an inorganic adsorptive medium in a non-polar solvent. This non-polar solvent can be the same solvent as for polymer extraction. The inorganic adsorptive medium selectively binds m-SWCNTs to further separate the sc-SWCNTs from the m-SWCNTs. The inorganic adsorptive medium and SWCNTs in the enriched sc-SWCNT dispersion may be present in a mass ratio of inorganic adsorptive medium to SWCNT of about 10:1 to 1000:1, or more preferably about 50:1 to 500:1. The inorganic adsorptive medium preferably comprises an inorganic oxide, for example silica (porous or non-porous), alumina, titania, a zeolite, a diatomaceous earth (e.g. Celite™) or mixtures thereof. The inorganic adsorptive medium may be functionalized to assist with specificity of reaction toward m-SWCNTs over sc-SWCNTs. Some suitable functional groups include, for example, cyano, amino, hydroxyl, mercapto, halo (F, Cl or Br), alkyl and aromatic groups. The inorganic adsorptive medium should be stable in non-polar solvents. The non-polar solvent may comprise an organic solvent, for example, an organic aromatic solvent. Some examples of non-polar solvents include, for example, toluene, benzene, ethyl benzene, xylenes, 1-methylnaphthalene and mixtures thereof. After mixing, the mixture is allowed to interact for a period of time from 5 min to 5 h, or from 10 to 60 min by using stirring, shaking or sonication. An example of sonication is bath sonication.

After exposing the enriched sc-SWCNT dispersion to the inorganic adsorptive medium, the sc-SWCNTs may be recovered by any suitable method, for example centrifugation, filtration and the like, or any combination thereof. The adsorbent enriched in m-SWCNTs is a solid that is easily collected in the sediment of a centrifugation process while the sc-SWCNTs remain dispersed in the supernatant. Further processing and isolation of the sc-SWCNTs may be accomplished by filtration and washing to remove free polymer. The recovered sc-SWCNTs have a conjugated polymer wrapping/coating and may be used in various applications including photovoltaic devices (PVDs), thin film transistors (TFTs), printable electronics and sensors.

The amine can be added to the enrichment step and/or the supernatant of a conventional CPE process, or the hybrid (two-step) CPE process, disclosed in, for example, WO 2015/024115 and Ding J, et al. *Nanoscale*. 2014, 6, 2328.

The addition of an amine compound into the CPE solution may mediate the interaction of the polymer with SWCNTs and thus enable the removal of excess polymer. The amine addition of may decrease the CP/CNT ratio from about 15:1 to about 0.75:1, which makes polymer removal easier and less costly. For example, triethylamine (TEA) can facilitate removal of a polymer wrapped around an SWCNT surface, at a concentration of 0.03%, with a resulting CP/SWCNT ratio of as low as 0.65.

Since addition of an amine during the enrichment step may reduce the purity of the sc-SWCNTs, an alternate method is to add the amine to the supernatant after the enrichment step, but prior to filtration. In this way, the purity is maintained while the CP/CNT ratio is reduced.

Examples of amines that may be used in this method are ethanolamine, pyridine and TEA. The effectiveness of the process was found to vary with the concentration of TEA used. For example, concentrations that are either very high or very low are not as effective at lowering the CP/CNT ratio.

Various objects, features, aspects and advantages of the inventive subject matter will become more apparent from the following detailed description of preferred embodiments, along with the accompanying drawing figures.

DETAILED DESCRIPTION OF PREFERRED EMBODIMENTS

Materials and Methods

Characterizations

Absorption spectra were collected on a UV-Vis-NIR spectrophotometer (Cary 5000, Varian) in a wavelength range from 300 to 2100 nm. A double beam mode was used with a pure solvent cuvette placed in the reference channel. Raman spectra were acquired with an InVia Raman microscope (Renishaw), using 514 nm (2.41 eV), 633 nm (1.96 eV), and 785 nm (1.58 eV) laser excitation sources and 50× magnification objective lens. Spectra were recorded in 100-3000 cm-1 region with a resolution of 4 cm-1. PLE mapping was done in a home-made system with a titanium-sapphire laser used as a wavelength tunable excitation with a tuning range from 720-1050 nm.

For yield and SWCNT concentration measurements, absorption spectroscopy was used. Yield is expressed as the mass percentage of sc-SWCNT in the enriched dispersion relative to the total mass of SWCNTs present in the raw material, which was calculated from thermogravimetric analyses (TGA) analysis. Principally, the yield value can be obtained by comparing the weight of sc-SWCNTs in the final product of the enrichment with the weight of starting raw material. But the final product is polymer wrapped/coated SWCNTs and therefore it is a mixture of polymer and SWCNTs. The polymer content in the final product has to be detected in order to evaluate the sc-SWCNT content. A spectroscopic approach is known in the art (Naumov—2011), which appears to be a more convenient method to simultaneously determine both the amount of polymer and sc-SWCNTs in the final product. Therefore, polymer and SWCNT concentration (mg/mL) of the enriched dispersions are calculated from their absorption spectra, and then the yield of the enrichment can be deduced.

Polyfluorene Derivatives

This example provides details of the preferred conjugated polymers.

Polyfluorenes with two alkyl groups at 9-position with a length from $C_8$ to $C_{18}$ were prepared by Suzuki reaction adapted from prior art methods (e.g. Ding 2002). The obtained polymers with the basic characterization data are listed in Scheme 1 and Table 1, where $Td^{1\%}$ and Tg were measured from thermogravimetric analyses (TGA) and differential scanning calorimetry (DSC).

Scheme 1-Structure of polyfluorenes

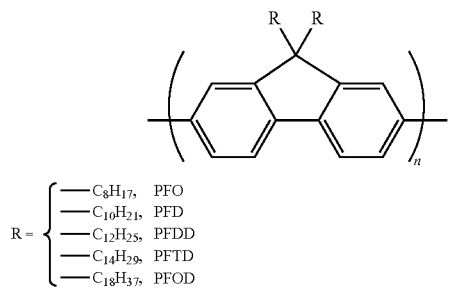

R = { —$C_8H_{17}$, PFO
      —$C_{10}H_{21}$, PFD
      —$C_{12}H_{25}$, PFDD
      —$C_{14}H_{29}$, PFTD
      —$C_{18}H_{37}$, PFOD }

TABLE 1

Characterization data of polyfluorenes

| Polymer | PFO(C8) | PFD(C10) | PFDD(C12) | PFTD(14) | PFOD(C18) |
|---|---|---|---|---|---|
| Mn (kDa) | 26.7 | 13.6 | 21.7 | 13.4 | 23.7 |
| PDI | 2.4 | 2.7 | 4.1 | 3.0 | 4.2 |
| Tg (° C.) | 136 | 101 | 48 | 40 | 35 |
| $Td^1$ % (° C.) | 390 | 380 | 381 | 374 | 382 |

EXAMPLE 1

Effect of TEA (Triethylamine) on a Large Scale Enrichment (50 Mg)

Figure 1:
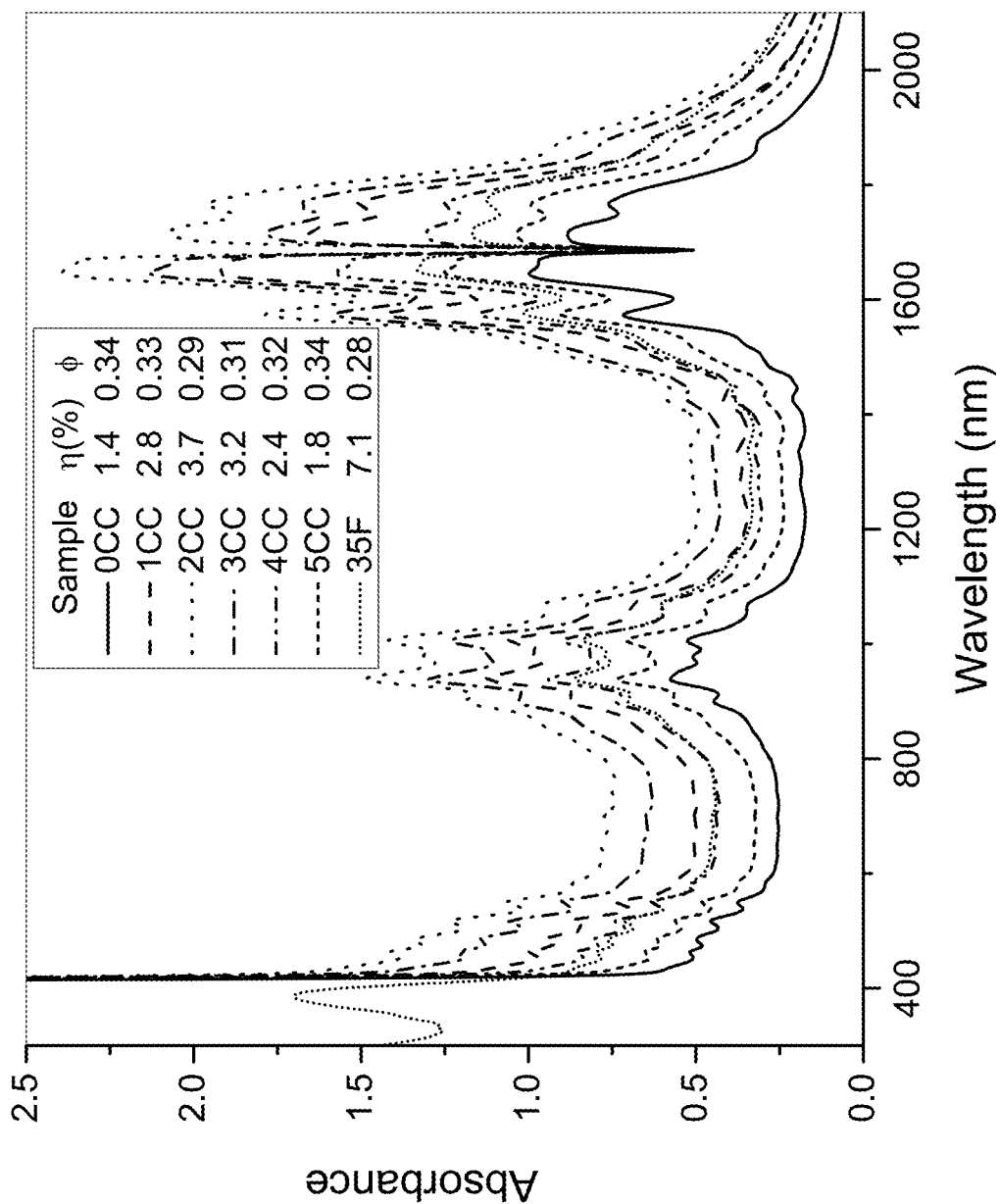
FIG. 1 shows UV spectra of supernatant from: a conditioning step, 1st, 2nd, 3rd, 4th, and 5th extraction of a CPE using PFDD; and the re-dispersed solution from the filtration of the combined supernatant of the 3rd, 4th, and 5th extraction (35F).

0.5% TEA was added into the conditioning step (to slightly de-dope nanotubes) of a standard CPE using PFDD as the conjugated polymer. A conditioning step (or pre-extraction) was followed by 5 successive PFDD extractions. The product from these extractions were marked as 0CC (conditioning) 1CC ($1^{St}$ extraction), 2CC ($2^{nd}$ extraction), 3CC ($3^{rd}$ extraction), 4CC ($4^{th}$ extraction), and 5CC ($5^{th}$ extraction). FIG. 1 displays the UV spectra of the supernatant from each extraction, with the yield ($\eta$) and the absorption peak ratio ($\phi$) values for each extraction is displayed in the inset. The absorption peak ratio ($\phi$) is defined as the ratio of the integrated area of the M11 and S22 peak envelop over the total area in this region. A high $\phi$, value reflects a high sc-SWCNT purity. In addition, the UV spectra of the re-dispersed solution from the filtration of 3CC, 4CC, and 5CC (Sample 35F) is also shown. It shows the PFDD/CNT ratio was easily reduced to 0.75 by filtration in the assistant of TEA. It should be noted that the yield of Sample 35F was calculated based on the weight of the film from the filtration.

FIG. 1 shows that the combined yield ($\eta$) of the conditioning step (0CC), the $1^{st}$ extraction (1CC) and $2^{nd}$ extraction (2CC) is more than double that of a CPE without the amine. However, the yield becomes quickly reduced in the successive extractions and this process results in a similar overall yield (~15%) for the 6 total extractions compared to a process without TEA. This result may be due to the low SWCNT content of the raw plasma tube sample, which is about 50%. The sc-SWCNT content in the raw plasma tube sample is about 33%. Therefore, a 15% yield means about half of the sc-SWCNTs (in the original raw plasma tube sample) have been extracted by this process.

It may be concluded that de-doping the SWCNTs with TEA can significantly promote the yield of the initial extraction—however, with lower sc-SWCNT purity. Overall, the addition of TEA in the conditioning step does not improve the total combined yield for a process with a set of 6 successive extractions. Therefore, if the goal is to achieve high purity and a high yield, a set of successive PFDD extractions without SWCNT de-doping (without TEA) is recommended. However, for an expedited process in which only one or two extractions are performed, the addition of TEA in a pre-conditioning step, provides a good yield.

FIG. 1 also shows a very low PFDD content of the sample from filtration (Sample 35F), based on the peak intensities of sample 35F at 385 nm and 938 nm. The PFDD/CNT value becomes only 0.75 after a simple rinsing process. A similar filtration in a standard CPE (i.e. without TEA) resulted in a PFDD/CNT ratio of about 15.0, about 20-fold larger than sample 35F.

EXAMPLE 2

Figure 2:
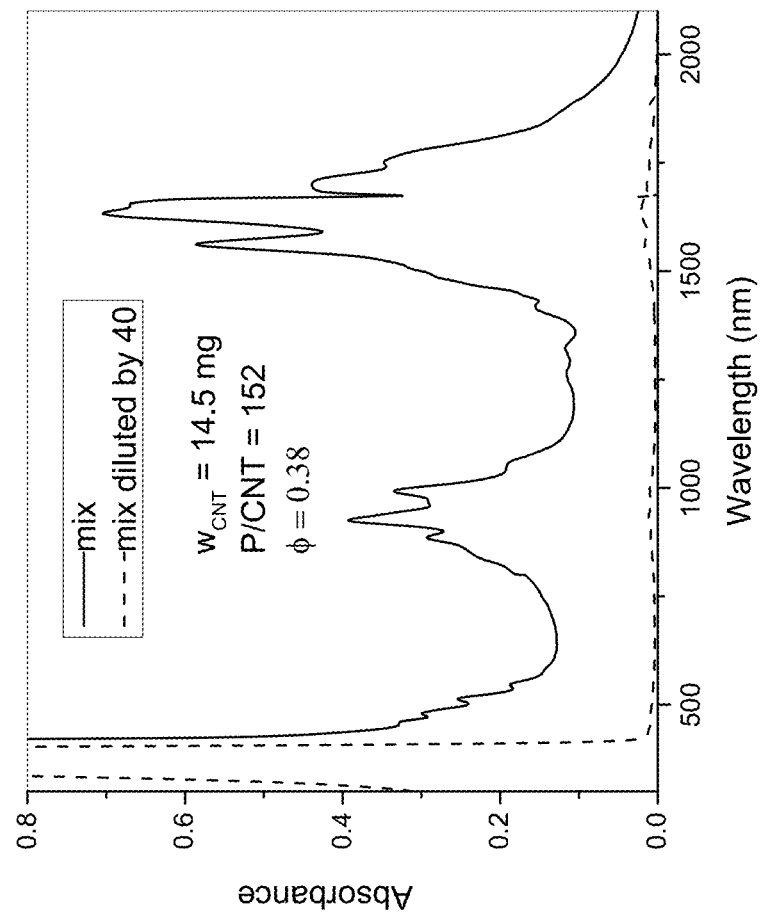
FIG. 2 shows UV spectra of a 1750 ml solution obtained from a PFDD extraction process that has been conducted by applying 5 successive extractions.

Effect of Different Amines on the Filtration of the Supernatant from Enrichment by PFDD Extraction In another set of experiments, different types of amines together with a strong base (NaOH) and a strong acid (HCl) have been tested for promoting the filtration of the supernatant from enrichment. For this purpose, a PFDD extraction process has been conducted by applying 5 successive extractions to produce 1750 mL of combined supernatant with the UV spectra and the relevant characterization data shown in FIG. 2.

Seven different 200 ml samples of this solution were set aside, with a different additive added to each sample: none (Control or CTR), water ($H_2O$), triethylamine (TEA), ethanol amine (EOA), pyridine (Py), NaOH and HCl. The amount of each additive is listed in Table 1. Each solution was then bath sonicated for 10 minutes to ensure good mixing, followed by filtration. The filtrate was rinsed with 10 mL of toluene three times. The composition of the resulting solid was then analyzed by UV spectroscopy.

TABLE 1

Treatment Condition And Filtration Results

| Sample | Before | None | H2O | NaOH | HCl | TEA | EOA | PY |
|---|---|---|---|---|---|---|---|---|
| $W_{Base}$ (mg)# | — | — | 10 | 10 | 10 | 63.6 | 38.5 | 49.8 |
| MW (g/mol) | — | — | — | — | — | 101 | 61.1 | 79.1 |
| $N_B$ (mmol)* | — | — | — | 0.063 | 0.063 | 0.63 | 0.63 | 0.63 |
| Time (min) | — | 270 | 270 | 600 | 70 | 55 | 160 | 180 |
| PFDD/CNT | 152 | 2.33 | 2.92 | 10.8 | 1.51 | 0.80 | 1.46 | 1.36 |

Note:
*the usage of the base is designed at the molar ratio of carbon/base of 1:4.5 for amines and 1:0.45 for NaOH.
6.3M NaOH and HCl solution were used.

The addition of the amine compound resulted in a clear solution, thereby indicating good mixing. However, after 10 mg of the NaOH solution was added into the sc-SWCNT dispersion, a white powder was formed. Sonication turned the solution a bit cloudy. Filtering the resulting solution took extremely long time (10 h). In order to check if this was due to the existence of fine NaOH powder blocking the filtration membrane, the obtained filtration cake was soaked in 30/70 (water/MeOH) solution for 3 hours and then dried and 12/17 of the solid was re-dispersed in 100 mL of toluene and filtered again. It took 180 min to complete, at the same level as the first filtration. The absorption spectrum of the redispersed resulting film showed a high PFDD/CNT ratio, indicating the low filtration speed is due to the high content of polymer which blocked the filtration. Therefore the extremely long filtration time and high PFDD/CNT ratio was due to the NaOH treatment. HCl treatment resulted in broad absorption peaks—an indicator of heavy doping of the nanotubes. The PFDD/CNT ratio was at a level similar to that of samples treated with EOA and Py.

Figure 3A:
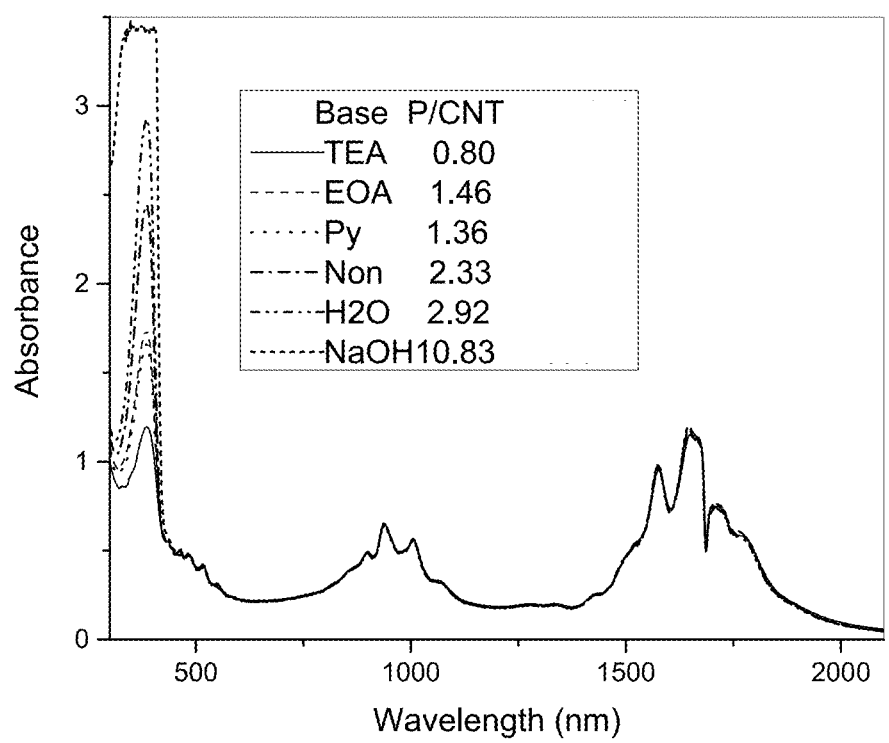
FIGS. 3A and 3B show UV spectra of re-dispersed solutions in the presence of difference additives.
Figure 3B:
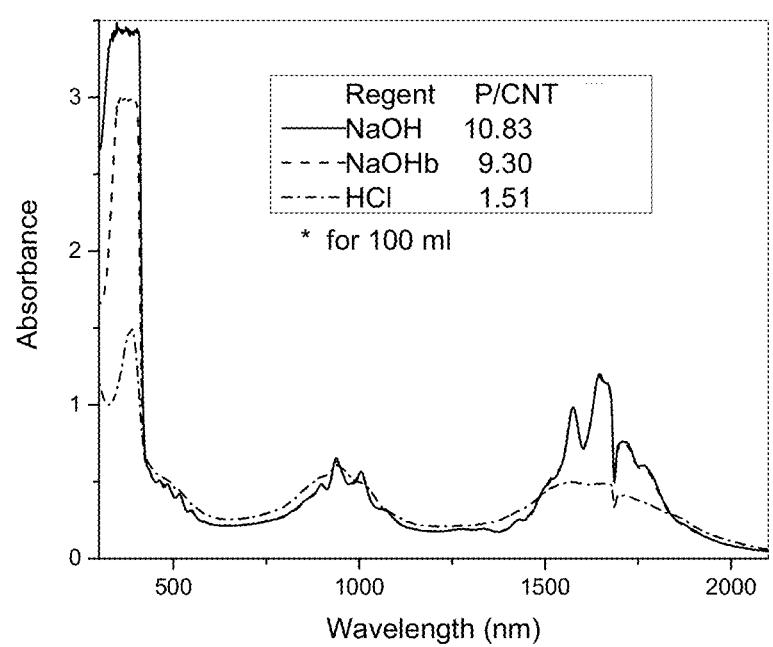
Figure 4:
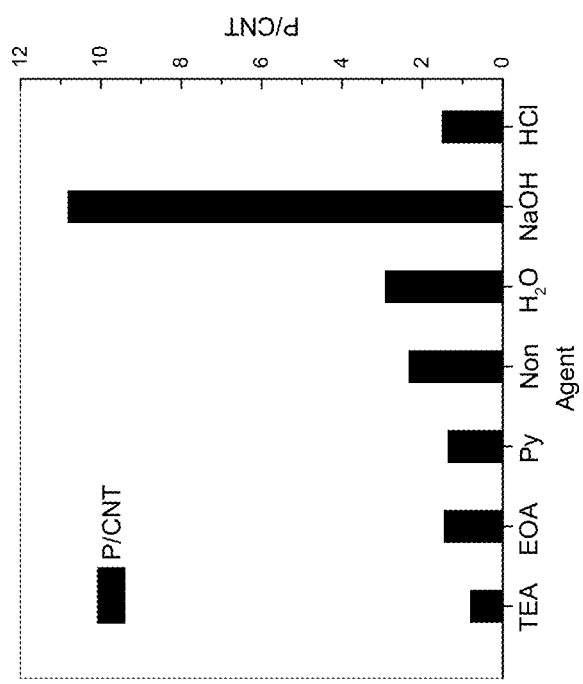
FIG. 4 illustrates the effect of different additives on the PFDD/CET ratio.

The UV spectra of the re-dispersed films from the filtrations using different additives is shown in FIGS. 3A and 3B, with the PFDD/CNT ratio listed in the inset. The effect of different additives to the PFDD/CNT ratio was also compared in FIG. 4. It can be seen that TEA is the most effective regent in removing the wrapping polymer to result in the lowest PFDD/CNT ratio, On the other hand, addition of NaOH showed a negative effect with an increased PFDD/CNT ratio.

EXAMPLE 3

Effect of TEA Concentration

Different amounts of TEA were added to 100 mL samples of combined supernatant, shown in Table 2, and then sonicated for 10 min. The solution was filtered, the filtration film was rinsed with 10 mL of toluene, and then was dispersed in toluene for UV spectroscopy analysis.

TABLE 2

The effect of TEA usage on the filtration of 100 mL of solution.

| Sample | Before | TEA-2 | TEA-3 | TEA-4 | TEA-5 |
|---|---|---|---|---|---|
| $W_{Base}$ (mg) | — | 320 | 60 | 30 | 10 |
| $N_B$ (mmol) | | | | | |
| Time (min) | | 90 | 70 | 60 | 80 |
| PFDD/CNT | | 1.8 | 1.06 | 0.89 | 1.19 |

Figure 5:
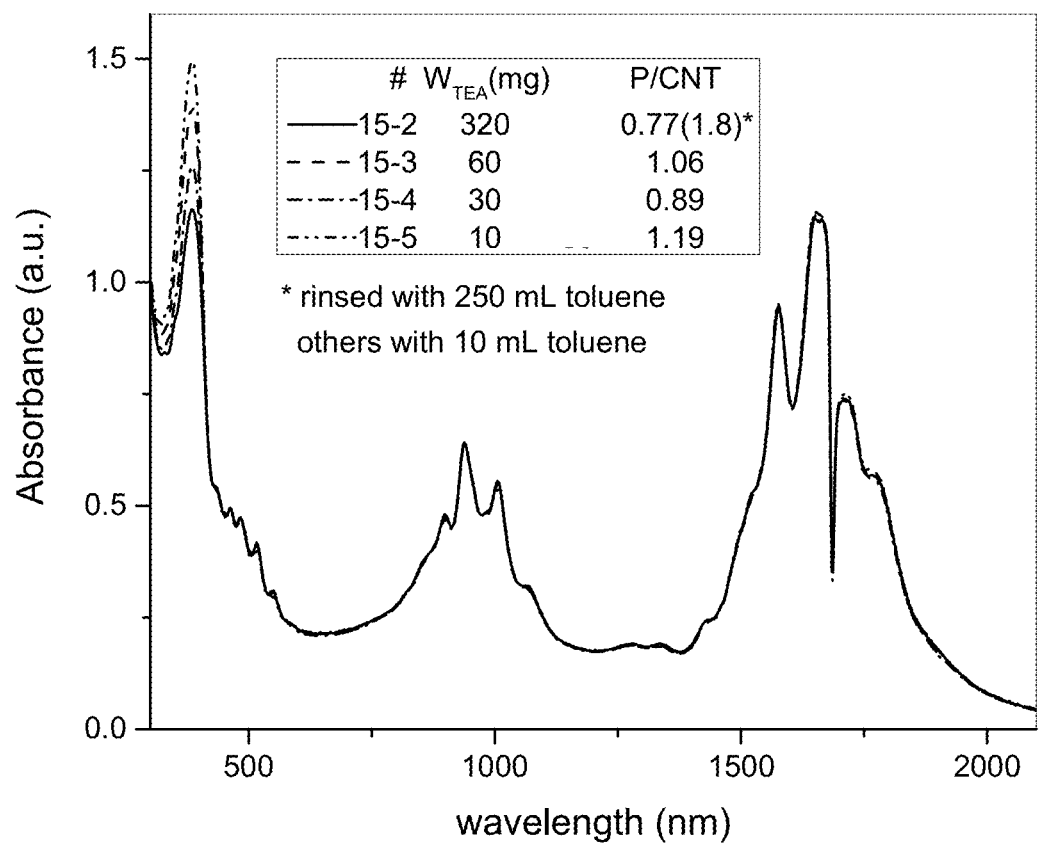
FIG. 5 shows UV spectra of re-dispersed solutions of TEA assisted filtration of the combined supernatant from PFDD extraction.
Figure 6:
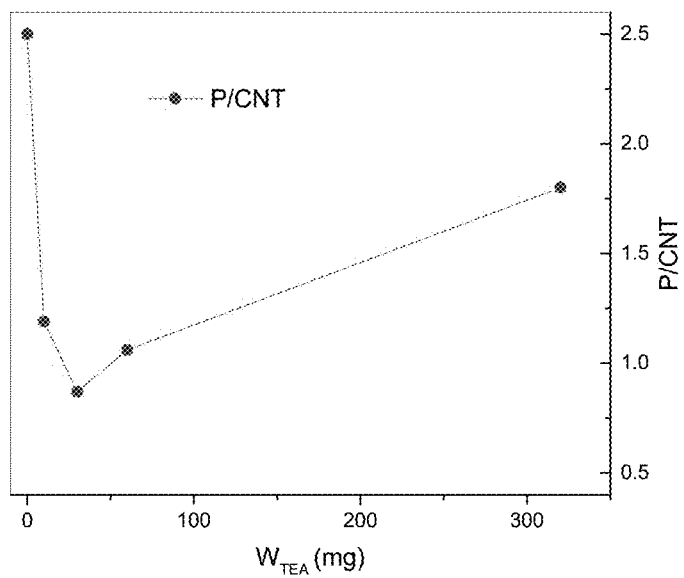
FIG. 6 illustrates influence of the TEA concentration on the PFDD/CNT ratio for 100 mL of the supernatant.

FIG. 5 displays the UV spectra of the re-dispersed filtration films with different amounts of TEA used of in the filtration. The influence of the TEA usage on the PFDD/CNT ratio is also shown in FIG. 6, in which 30 mg TEA per 100 mL of the solution (corresponding to a TEA/SWCNT ratio of 4.3:1) gives the best performance in reducing the PFDD/CNT ratio.

EXAMPLE 4

Figure 7:
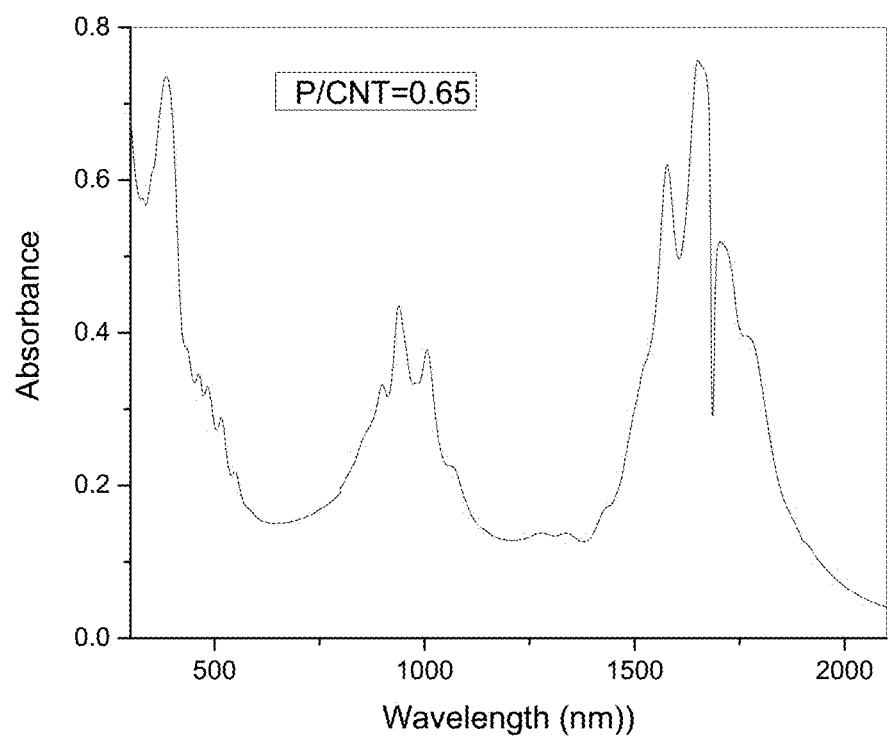
FIG. 7 shows the UV spectrum of the re-dispersed film from TEA assisted filtration after large quantity solvent rinsing.

Limit on the Removal of the Wrapping Polymer by TEA Assisted Filtration and Rinsing 63 mg of TEA was added to 200 mL of combined supernatant, sonicated for 10 min and then filtered. The filtration film was then rinsed with 200 mL of toluene 3 times, and then dispersed in toluene. The UV spectrum of the resulting sample is shown in FIG. 7, which indicates a PFDD/CNT ratio of 0.65, which was one of the lowest PFDD/CNT ratios observed.

Of course, it should be appreciated that the above examples only provide an illustration of the inventive subject matter and should not be deemed limiting. Thus, specific embodiments and applications of methods have been disclosed. It should be apparent to those skilled in the art that many more modifications besides those already described are possible without departing from the inventive concepts herein. The inventive subject matter, therefore, is not to be restricted except in the spirit of the appended claims.

Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

REFERENCES

The contents of the entirety of each of which are incorporated by reference.

Jianfu Ding, Zhao Li, Jacques Lefebvre, Fuyong Cheng, Girjesh Dubey, Shan Zou, Paul Finnie, Amy Hrdina, Ludmila Scoles, Gregory P. Lopinski, Christopher T. Kingston, Benoit Simard, Patrick R. L. Malenfant, "Enrichment of large-diameter semiconducting SWCNTs by polyfluorene extraction for high network density thin film transistors", *Nanoscale*, 2014, 6, 2328-2339.

Jianfu Ding, Zhao Li, Jacques Lefebvre, Fuyong Cheng, Jeffrey L Dunford, Patrick R L Malenfant, Jefford Humes, Jens Kroeger, "A hybrid enrichment process combining conjugated polymer extraction and silica gel adsorption for high purity semiconducting single-walled carbon nanotubes (SWCNT)", *Nanoscale* 2015, 7 (38), 15741-15747.

Jianfu Ding, Zhao Li, Fuyong Cheng, Benoit Simard, Patrick R. L. Malenfant, Process for purifying semiconducting single-walled carbon nanotubes, U.S. provisional patent application 61/867,630 and WO 2015024115 A1.

The invention claimed is:

1. A process for selectively dispersing semi-conducting single-walled carbon nanotubes (sc-SWCNTs) in a solvent, the process comprising adding an amine to a supernatant from
a conjugated polymer extraction process (CPE) of the sc-SWCNTs,
wherein the amine partially displaces the conjugate polymer associated with the sc-SWNTs dispersed in the solvent.

2. The process of claim 1, wherein filtration of the sc-SWCNTs dispersed in the solvent takes less time than filtration of dispersed sc-SWNTs prepared by the CPE without the amine.

3. The process of claim 1, wherein the amine is a non-functionalized amine.

4. The process of claim 1, wherein the amine is an alkylamine.

5. The process of claim 1, wherein the amine is triethylamine, ethanol amine or pyridine.

6. The process of claim 1, wherein the conjugated polymer comprises a polyfluorene.

7. The process according to claim 6, wherein the polyfluorene is a 9,9-dialkyl-substituted polyfluorene or a 9,9-diC$_{8-36}$-alkyl-substituted polyfluorene.

8. The process according to claim 1, wherein the conjugated polymer comprises a. polythiophene.

9. The process according to claim 8, wherein the polythiophene is a 3-alkyl-substituted polythiophene or a 3-C$_{8-18}$-alkyl-substituted polythiophene.

10. The process according to claim 1, wherein the conjugated polymer comprises a copolymer of 3-C$_{10-18}$-alkyl-substituted thiophene with one or more comonomer units, the co-monomer comprising one or more of fluorene, bithiophene, phenylene, bipyridine, carbazole, anthracene, naphthalene or benzothiadiazole.

11. The process according to claim 1, wherein the conjugated polymer has a number average molecular weight greater than about 10,000 Da.

12. The process of claim 1, wherein the solvent is a non-polar solvent.

13. The process of claim 1, wherein the solvent comprises an aromatic organic solvent.

14. The process of claim 1, wherein the solvent comprises toluene, benzene, ethyl benzene, xylenes, 10methylnaphtalene or mixtures thereof.

15. A process for selectively dispersing semi-conducting single-walled carbon nanotubes (sc-SWCNTs) in a solvent, the process comprising adding an amine to a supernatant from
a conjugated polymer extraction process (CPE) of the sc-SWCNTs,
with the proviso that the amine excludes EDTA.

16. A process for displacement of a conjugated polymer from the surface of semi-conducting single-walled carbon nanotubes (sc-SWCNTs) dispersed in a solvent, the process comprising adding an amine to a supernatant from
a cojugated polymer extraction process (CPE) of the sc-SWCNTs.

17. A process for selectively dispersing semi-conducting single-walled carbon nanotubes (sc-SWCNTs) in a solvent, the process comprising adding an amine either:
a) to a conjugated polymer extraction process (CPE) of the sc-SWCNTs; or
b) after the CPE of the sc-SWCNTs
wherein the amine partially displaces the conjugate to polymer associated with the sc-SWNTs dispersed in the solvent, and
wherein the concentration of the amine is from 1 ppm to 0.1% by weight.

* * * * *